United States Patent [19]

Flynn

[11] Patent Number: 5,502,253
[45] Date of Patent: Mar. 26, 1996

US005502253A

[54] CYCLOHEX-2-ENYL ACETAMIDES

[75] Inventor: Gary A. Flynn, Cincinnati, Ohio

[73] Assignee: Merrell Pharmaceuticals Inc.

[21] Appl. No.: 415,028

[22] Filed: Mar. 30, 1995

Related U.S. Application Data

[63] Continuation of Ser. No. 155,972, Nov. 19, 1993, abandoned.

[51] Int. Cl.$^6$ .................................................. C07C 233/14
[52] U.S. Cl. .......................... 564/210; 564/462; 546/272
[58] Field of Search .............................................. 564/210

[56] References Cited

U.S. PATENT DOCUMENTS

| | | | |
|---|---|---|---|
| 4,608,082 | 8/1986 | Craig et al. | 558/49 |
| 4,824,832 | 4/1989 | Flynn et al. | 514/214 |
| 4,973,585 | 11/1990 | Flynn et al. | 514/214 |

FOREIGN PATENT DOCUMENTS 0249223  12/1987  European Pat. Off. .

OTHER PUBLICATIONS

Gary A. Flynn et al, *J. Am. Chem. Soc.*, 1987, vol. 109, p. 7914.

Gary A. Flynn et al, *Peptide Chemistry*, 1987, pp. 631–636.

M. F. Grenier—Loustalot et al, *Synthesis*, Communications Jan. 1976.

David J. Mathre et al, *J. Org. Chem.* 1991, vol. 56 pp. 751–762.

Flynn et al., *J. Med. Chem.* 1993, 36 2420–2423.

*Primary Examiner*—Jane Fan
*Attorney, Agent, or Firm*—David M. Stemerick

[57] ABSTRACT

The present invention relates to a novel enantiospecific process for preparing (S)-1-[2(S)-(1,3-dihydro-1,3-dioxo-isoindo-2-yl)-1-oxo-3-phenylpropyl] -1,2,3,4-tetrahydro-2-pyridine-carboxylic acid methyl ester which is a useful intermediate in the preparation of [4S-[ 4α, 7α(R*), 12bβ] ]-7-[(1-oxo-2(S)-thio-3-phenylpropyl)amino] -1,2,3,4,6,7,8, 12b-octahydro-6-oxo-pyrido[ 2,1-a][2]benzazepine-4-carboxylic acid and [4S-[4α, 7α(R*), 12bβ]]-7-[(1-oxo-2(S)-acetylthio-3-phenylpropyl)amino] -1,2,3,4,6,7,8,12b-octahydro-6-oxo-pyrido[ 2,1-a][2]benzazepine-4-carboxylic acid and pharmaceutically acceptable salts thereof which is useful as an inhibitor of enkephalinase and angiotensin converting enzyme and to novel intermediates thereof.

2 Claims, No Drawings

CYCLOHEX-2-ENYL ACETAMIDES

This is a continuation of application Ser. No. 08/155,972, filed Nov. 19, 1993, now abandoned which is herein incorporated by reference.

BACKGROUND OF THE INVENTION

The present invention relates to a novel process for preparing (S)-1-[2(S)-(1,3-dihydro-1,3-dioxo-isoindo-2-yl)-1-oxo-3-phenylpropyl]-1,2,3,4-tetrahydro-2-pyridine-carboxylic acid methyl ester which is a useful intermediate in the preparation of [4S-[4α, 7α(R*), 12bβ]]-7-[(1-oxo- 2(S)-thio-3-phenylpropyl)amino]-1,2,3,4,6,7,8,12b-octahydro-6-oxo-pyrido[2,1-a][2]benzazepine-4-carboxylic acid and [4S-[4α, 7α(R*), 12bβ]]-7-[(1-oxo-2(S)-acetylthio- 3-phenylpropyl)amino]-1,2,3,4,6,7,8,12b-octahydro-6-oxo-pyrido[ 2,1-a][2]benzazepine-4-carboxylic acid and pharmaceutically acceptable salts thereof which are useful as inhibitors of enkephalinase and angiotensin converting enzyme [European Patent Application No. 0 481 522 A1, published 22 Apr. 1992] and to novel intermediates thereof.

The process and intermediates of the present invention provide a novel enantiospecific method for preparing (S)-1-[2(S)-(1,3-dihydro-1,3-dioxo-isoindo-2-yl)-1-oxo-3-phenyl-propyl] -1,2,3,4-tetrahydro-2-pyridine-carboxylic acid methyl ester.

SUMMARY OF THE INVENTION

The present invention provides a novel process for preparing (S)-1-[2(S)-(1,3-dihydro-1,3-dioxo-isoindo-2-yl)-1-oxo-3-phenylpropyl]-1,2,3,4-tetrahydro-2-pyridine-carboxylic acid methyl ester comprising the steps of:

(a) reacting cyclohexenone sequentially with an appropriate chlorinating agent and an appropriate base to give 2-chlorocyclohex-2-en-1-one;

(b) reacting 2-chlorocyclohex-2-en-1-one with an appropriate chiral auxiliary and an appropriate reducing agent to give (R)-2-chloro-cyclohex-2-enylalcohol;

(c) reacting (R)-2-chloro-cyclohex-2-enylalcohol with trichloroacetonitrile to give (R)-2,2,2-trichloro-1-(2-chloro-cyclohex- 2-enyloxy)-ethylideneamine;

(d) reacting (R)-2,2,2-trichloro-1-(2-chloro-cyclohex-2-enyloxy)-ethylideneamine with heat to give (S)-2,2,2-trichloro-N-( 2-chloro-cyclohex-2-enyl)-acetamide;

(e) reacting (S)-2,2,2-trichloro-N-(2-chloro-cyclohex-2-enyl)-acetamide with an appropriate solvolysis agent to give (S)-2-chloro-cyclohex-2-enylamine;

(f) reacting (S)-2-chloro-cyclohex-2-enylamine with phthalimido-L-phenyalanine derivative to give (S)-N-(2-chloro-cyclohex- 2-enyl)-2-[2(S)-1,3-dihydro-1,3-dioxo-isoindol-2-yl]-3-phenyl-propionamide;

(g) reacting (S)-N-(2-chloro-cyclohex-2-enyl)-2-[2(S)-1,3-dihydro-1,3-dioxo-isoindol-2-yl]-3-phenyl-propionamide with ozone in the presence of methanol to give after a reductive work-up N-[2(S)-[(6-oxo)-hexanoic acid methyl ester]]-2-[2(S)-1,3-dihydro-1,3-dioxo-isoindol- 2-yl]-3-phenyl-propionamide methyl ester;

(h) reacting N-[2(S)-[(6-oxo)-hexanoic acid methyl ester]]-2-[2(S)-1,3-dihydro-1,3-dioxo-isoindol-2-yl]-3-phenyl-propionamide with an appropriate cyclizing acid.

In addition, the present invention provides novel intermediates of the formula:

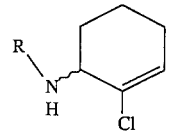

wherein
R is hydrogen or trichloroacetyl.

DETAILED DESCRIPTION OF THE INVENTION

As used in this application:

a) the designation "▬▬" refers to a bond that protrudes forward out of the plane of the page;

b) the designation " ||||||||··· " refers to a bond that protrudes backward out of the plane of the page;

c) the designation "〜〜〜" refers to a bond for which the stereochemistry is not designated;

d) the term "pharmaceutically acceptable salts" refers to either acid addition salts or to base addition salts.

The expression "pharmaceutically acceptable acid addition salts" is intended to apply to any non-toxic organic or inorganic acid addition salt of [4S-[4α, 7α(R*), 12bβ]]-7-[(1-oxo-2(S)-thio-3-phenylpropyl)amino]-1,2,3,4,6,7,8,12b-octahydro-6-oxo-pyrido[2,1-a][2]benzazepine-4-carboxylic acid or [4S-[4α, 7α(R*), 12bβ]]-7-[(1-oxo-2(S)-acetylthio-3-phenylpropyl)amino] -1,2,3,4,6,7,8,12b-octahydro-6-oxo-pyrido[ 2,1-a][2]benzazepine-4-carboxylic acid or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, and sulfonic acids such as p-toluenesulfonic acid, methane sulfonic acid and 2-hydroxyethane sulfonic acid. Such salts can exist in either a hydrated or substantially anhydrous form.

The expression "pharmaceutically acceptable basic addition salts" is intended to apply to any non-toxic organic or inorganic basic addition salts of [4S-[4α, 7α(R*), 12bβ]]-7-[(1-oxo-2(S)-thio-3-phenylpropyl)amino]- 1,2,3,4,6,7,8, 12b-octahydro-6-oxo-pyrido[2,1-a] [2]benzazepine-4-carboxylic acid or [4S-[4α, 7α(R*), 12bβ]]-7-[(1-oxo-2(S)-acetylthio-3-phenylpropyl)amino]-1,2,3,4,6,7,8,12b-octahydro-6-oxo-pyrido[2,1-a] [2]benzazepine-4-carboxylic acid or any of its intermediates. Illustrative bases which form suitable salts include alkali metal or alkaline-earth metal hydroxides such as sodium, potassium, calcium, magnesium, or barium hydroxides; ammonia, and aliphatic, cyclic, or aromatic organic amines such as methylamine, dimethylamine, trimethylamine, triethylamine, diethylamine, isopropyldiethylamine, pyridine and picoline.

As is appreciated by one of ordinary skill in the art the methodology disclosed in this application can be used to prepare all the enantiomers and all the diastereomers of (S)-1-[2(S)-(1,3-dihydro-1,3-dioxo-isoindo-2-yl)-1-oxo-3-phenylpropyl] -1,2,3,4-tetrahydro-2-pyridine-carboxylic acid methyl ester and thereby the enantiomers and diastereomers of the inhibitor of enkephalinase and angiotensin converting enzyme produced therefrom. The stereoisomer of (S)-1-[2(S)-( 1,3-dihydro-1,3-dioxo-isoindo-2-yl)-1-oxo-3-phenylpropyl]- 1,2,3,4-tetrahydro-2-pyridine-carboxylic acid methyl ester which is formed by the present invention depends on the stereochemistry of 2-chloro-cyclohex-2-enylamine and the stereochemistry of the phthalimido-phenylalanine derivative.

A general synthetic procedure is set forth in Scheme A. In Scheme A, all substituents unless otherwise indicated, are as previously defined. Starting materials, reagents, techniques, and procedures used in Scheme A are well known and appreciated by one of ordinary skill in the art.

over chlorination products. The reaction is carried out at temperatures of from −40° C. to 20° C., with a temperature of from −5° C. to 0° C. preferred. The product may be isolated from the reaction zone by extraction and evaporation, as is well known in the art. The product may be purified by techniques well known in the art, such as chromatography and recrystallization.

In Scheme A step b, 2-chlorocyclohex-2-en-1-one is contacted with an appropriate chiral auxiliary and an appropriate reducing agent to give (R)-2-chloro-cyclohex-2-enylalcohol.

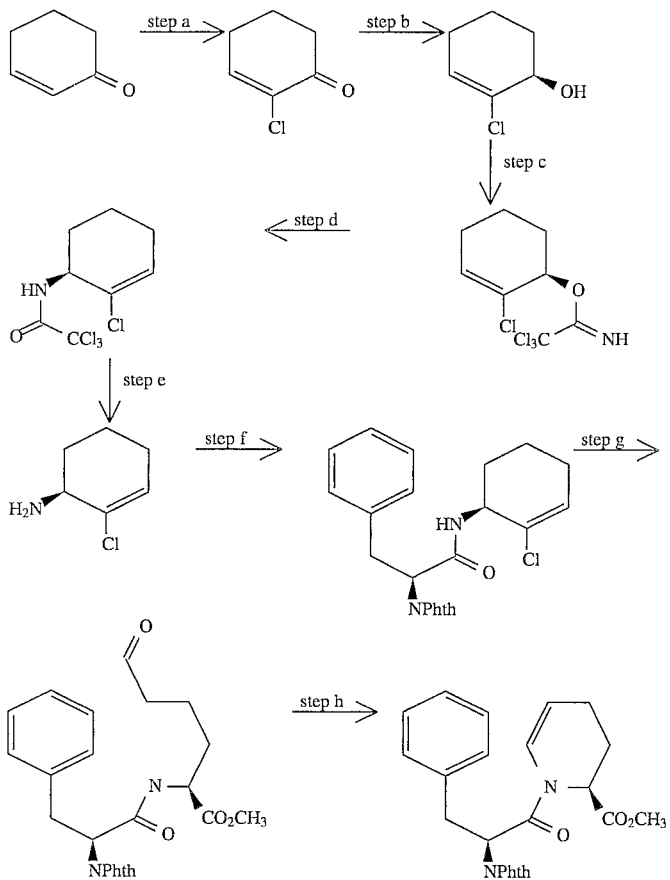

SCHEME A

In Scheme A step a, cyclohexenone is sequentially contacted with an appropriate chlorinating agent and an appropriate base to give 2-chlorocyclohex-2-en-1-one.

An appropriate chlorinating agent is one that may provide the proposed 2,3-dichlorocyclohexan-1-one intermediate without giving rise to inconvenient amounts of over chlorination products. 2,3-Dichlorocyclohexan-1-one is proposed in the art to be the intermediate in step a. It is intended that the present invention is not limited in any way by the proposal in the art of 2,3-dichlorocyclohexan- 1-one as the intermediate in step a.

An appropriate base is one which assists in the elimination of the 3-position chlorine without the formation of by-products of nucleophilic attack.

For example, cyclohexenone is contacted with an equimolar amount of an appropriate chlorinating agent. The reaction is carried out in a suitable solvent, such as dichloromethane. The use of a hindered base, such as 2,6-lutidine during the chlorination is advantageous in preventing the formation of An appropriate chiral auxiliary is one that leads stereoselective reduction of 2-chlorocyclohex-2-en-1-one.

An appropriate reducing agent is one which participates in formation of a chiral complex with an appropriate chiral auxiliary to give a stereoselectively reduced product. Appropriate reducing agents are well known in the art and include but are not limited to borane tetrahydrofuran complex, and borane dimethyl sulfide complex, with borane dimethyl sulfide complex being preferred.

For example, 2-chlorocyclohex-2-en-1-one is contacted with a fractional molar amount of an appropriate chiral auxiliary, such as (S)-tetrahydro-1-methy-3,3-diphenyl-1H,3H-pyrrolo-[1,2C][1,3,2]oxazaborole [D. J. Mathre et al., J. Org. Chem. 56, 751–762 (1991)] and a slight molar excess of an appropriate reducing agent. The amount of appropriate chiral auxiliary depends on the chiral auxiliary used and ranges from 0.05 to 0.5 molar equivalents. The reaction is carried out at a temperature that does not allow for the over reduction of the enone function and allows for the enantioselective reduction of the chiral auxiliary complex. The reaction is carried out in a suitable solvent, such as tetrahydrofuran or diethyl ether. The product may be isolated from the reaction zone by quenching the reaction with a protic solvent, such as methanol and extraction. The product may be used without further purification or may be purifying by methods well known in the art, such as chromatography and recrystallization.

In Scheme A step c, (R)-2-chloro-cyclohex-2-enylalcohol is contacted with trichloroacetonitrile to give (R)-2,2,2-trichloro- 1-(2-chloro-cyclohex-2-enyloxy)-ethylideneamine.

For example, (R)-2-chloro-cyclohex-2-enylalcohol is contacted with a molar excess of trichloroacetonitrile. The reaction is carried in the presence of a catalytic amount of a base, such as sodium hydride. A catalytic amount varies from 0.05 to 0.20 molar equivalents. The reaction is carried out in a suitable solvent, such as tetrahydrofuran or diethyl ether. The reaction is carried out at temperatures of from −20° C. to 20° C., with 0° C. being preferred. The product may be isolated from the reaction zone by evaporation or extraction and may be used without further purification or may be purifying by methods well known in the art, such as chromatography and recrystallization.

In Scheme A step d, (R)-2,2,2-trichloro-1-(2-chloro-cyclohex- 2-enyloxy)-ethylideneamine is heated to give (S)-2,2,2-trichloro-N-(2-chloro-cyclohex-2-enyl)-acetamide.

For example, (R)-2,2,2-trichloro-1-(2-chloro-cyclohex-2-enyloxy)-ethylideneamine is heated at a temperature of from 130° C. to 150° C. The reaction is carried out in a suitable solvent, such as chlorobenzene. The product may be isolated from the reaction zone by evaporation or extraction and may be purifying by methods well known in the art, such as chromatography and recrystallization.

In Scheme A step e, (R)-2,2,2-trichloro-N-(2-chloro-cyclohex- 2-enyl)-acetamide is treated with an appropriate solvolyzing agent to give (S)-2-chloro-cyclohex-2-enylamine.

Appropriate solvolysis agents are well known in the art, such as methanol, ethanol, and water.

For example, (S)-2,2,2-trichloro-N-(2-chloro-cyclohex-2-enyl)-acetamide is contacted with water to give (S)-2-chloro-cyclohex- 2-enylamine. The reaction may be carried out in a suitable solvent, such as ethanol, methanol, water, methanol/water mixtures, or ethanol/water mixtures. The reaction is promoted by the addition of a suitable base, such as potassium carbonate. The reaction is carried out at a temperature of from 50° C. to 90° C. with 70° C. being preferred. The product may be used directly. When methanol/water mixtures or ethanol/water mixtures are used the product may be used directly after the removal of the alcohol solvent. The product may be isolated from the reaction zone by evaporation or extraction and may be used without further purification or may be purifying by methods well known in the art, such as chromatography and salt formation and recrystallization.

In Scheme A step f, (S)-2-chloro-cyclohex-2-enylamine is reacted with an appropriate phthalimido-L-phenylalanine derivative to give (S)-N-(2-chloro-cyclohex-2-enyl)-2-[ 2(S)-1,3-dihydro-1,3-dioxo-isoindol-2-yl)-3-phenyl-propionamide.

An appropriate phthalimido-L-phenylalanine derivative is one that transfers the phthalimido-L-phenylalanine group, such as phthalimido-L-phenylalanine acid, phthalimido-L-phenylalanine acid anhydride, a phthalimido-L-phenylalanine acid mixed anhydride, phthalimido-L-phenylalanine acid chloride, or phthalimido-L-phenylalanine N-hydroxysuccinimide.

For example, (S)-2-chloro-cyclohex-2-enylamine is contacted with an appropriate phthalimido-L-phenyalanine derivative. When the phthalimido-L-phenyalanine acid the reaction is carried out in the presence of a reagent that assists in the coupling of acids and amines, such as 1,3-dicyclohexylcarbodiimide or 2-ethyl-1-ethoxycarbonyl-1,2-dihydroquinoline. When the appropriate phthalimido-L-phenyalanine derivative is phthalimido-L-phenyalanine acid anhydride, a phthalimido-L-phenyalanine acid mixed anhydride, phthalimido-L-phenyalanine acid chloride, or phthalimido-L-phenyalanine N-hydroxysuccinimide the reaction is carried out in the presence of a base, such as sodium carbonate, sodium bicarbonate, potassium carbonate, triethylamine, or potassium bicarbonate to neutralize the acid which is liberated during the course of the reaction. The reaction is carried out in suitable solvent, such as water, tetrahydrofuran, ethyl acetate, or ethyl acetate/water mixtures. The reaction is carried out at a temperature of from −20° C. to 40° C., with 0° C. being preferred. The product may be isolated from the reaction zone by extraction and evaporation, as is well known in the art. The product may be purified by techniques well known in the art, such as chromatography and recrystallization.

In Scheme A step g, (S)-N-(2-chloro-cyclohex-2-enyl)-2-[ 2(S)-1,3-dihydro-1,3-dioxo-isoindol-2-yl)-3-phenyl-propionamide is contacted with ozone in the presence of methanol to give after a reductive work-up N-[2(S)-[(6-oxo)-hexanoic acid methyl ester]]-2-[2(S)-1,3-dihydro-1,3-dioxo-isoindol-2-yl)-3-phenyl-propionamide methyl ester.

For example, (S)-N-(2-chloro-cyclohex-2-enyl)-2-[2(S)-1,3-dihydro-1,3-dioxo-isoindol-2-yl)-3-phenyl-propionamide is contacted with ozone in the presence of methanol. The reaction is carried out in a suitable solvent, such as dichloromethane. The reaction is carried out at a temperature of from −100° C. to −60° C., with −70° C. being preferred. The reaction is worked-up reductively by the addition of a suitable reducing agent, such as tributylphosphine or dimethyl sulfide. The product may be isolated from the reaction zone by evaporation and may be used without further purification. The product may be purified by techniques well known in the art, such as chromatography and recrystallization.

In Scheme A step h, N-[2(S)-[(6-oxo)-hexanoic acid methyl ester]]-2-[2(S)-1,3-dihydro-1,3-dioxo-isoindol-2-yl-3-phenyl-propionamide is contacted with an appropriate cyclizing acid to give (S)-1-[2(S)-(1,3-dihydro- 1,3-dioxo-isoindo-2-yl)-1-oxo-3-phenylpropyl]- 1,2,3,4-tetrahydro-2-pyridine-carboxylic acid methyl ester.

For example, N-[2(S)-[(6-oxo)-hexanoic acid methyl ester]]-2-[2(S)-1,3-dihydro-1,3-dioxo-isoindol-2-yl)-3-phenyl-propionamide phenyl-propionamide is contacted with an appropriate cyclizing acid, such as trifluoroacetic acid. The reaction is carried out in a suitable aprotic solvent, such as methylene chloride. The reaction is carried out at the reflux temperature of the solvent. The reaction is carried out in such a way that the refluxate can be dried as it is formed, such as by the use of a Dean-Stark trap or by passing the refluxate through a bed of 3Å or 4Å molecular sieves. The product may be isolated by evaporation and may be purified by techniques well known in the art, such as chromatography and recrystallization.

The following examples present typical syntheses as described in Scheme A. These examples are understood to be illustrative only and are not intended to limit the scope of the invention in any way. As used in the following examples, the following terms have the meanings indicated: "g" refers to grams, "mg" refers to milligrams, "mmol" refers to millimoles, "mL" refers to milliliters, "μL" refers to microliters, "° C." refers to degrees Celsius, "$R_f$" refers to retention factor, "mp" refers to melting point, "dec" refers to decomposition, "$[\alpha]^2{}_D{}^0$" refer to specific rotation of the D line of sodium at 20° C. obtained in a 1 decimeter cell, "c" refers to concentration in g/mL, "M" refers to molar, "L" refers to liter, "MeOH" refers to methanol, "2-PrOH" refers to isopropanol, "DIAD" refers to diisopropyl azodicarboxylate, and "TLC" refers to thin layer chromatography.

EXAMPLE 1

Scheme A, Step a:

2-Chlorocylcohexeneone

Combine cyclohexenone (19.2 g, 200 mmol) and dichloromethane (75 mL). Place under an inert atmosphere. Cool the solution to −10° C. Prepare a solution of sulfuryl chloride (17.0 mL, 200 mmol) in dichloromethane (30 mL). Add 3 mL of the sulfuryl chloride solution to the cooled solution above. Add 2,6-lutidine (1.0 mL, 10 mmol). Add the remainder of the sulfuryl chloride solution at such a rate that the temperature of the reaction mixture remains between −10° C. and 0° C. Stir at −10° C. for 15 minutes after the sulfuryl chloride addition is complete. Add triethyl amine (30 mL, 215 mmol) in dichloromethane (20 mL) keeping the temperature of the reaction mixture below 0° C. Warm to 0° C. and stir for 30 minutes. Dilute with dichloromethane (200 mL) and extract with 10% hydrochloric acid solution, saturated sodium bicarbonate solution, and saturated sodium chloride solution. Dry the separated organic layer over $MgSO_4$, filter and evaporate in vacuo to give a solid. Recrystallize the solid from hexane to give the title compound as a solid: mp; 70°–72° C.

EXAMPLE 2

Scheme A, Step b:

(R)-2-Chloro-cyclohex-2-enylalcohol

Combine 2-chlorocylcohexeneone (20.77 g, 160 mmol) and (S)-tetrahydro-1-methy-3,3-diphenyl-1H,3H-pyrrolo-[1,2C][1,3,2]oxazaborole (13 mmol) [prepared by the method of D. J. Mathre et al., *J. Org. Chem.* 56, 751–762 (1991)] in tetrahydrofuran (150 mL). Cool to −5° C. and add borane dimethyl sulfide complex (50 mL, 2M in tetrahydrofuran, 100 mmol) over 30 minutes. Stir the solution at −5° C. for 3 hours. Add methanol (5 mL) and stir until gas evolution ceases. Add methanol (100 mL) and stir at ambient temperature for 12 hours. Evaporate in vacuo to give a residue. Partition the residue between dichloromethane and 10% hydrochloric acid solution. Separate the organic layer and extract with saturated sodium bicarbonate solution. Dry the separated organic layer over $MgSO_4$, filter and evaporate in vacuo to give the title compound as an oil which can be used without further purification.

EXAMPLE 3

Scheme A, Step c:

(R)-2,2,2-Trichloro-1-(2-chloro-cyclohex-2-enyloxy)-ethylideneamine

Combine sodium hydride (0.50 g, 60% in oil, 12 mmol) and diethyl ether (50 mL) and cool to 0° C. Add over 15 minutes a solution of (R)-2-chloro-cyclohex-2-enylalcohol (23.0 g, 160 mmol) in diethyl ether (40 mL). Stir until gas evolution ceases. Add a solution of trichloroacetonitrile (20 mL, 200 mmol) in diethyl ether (30 mL). Stir at 0° C. for 30 minutes and then warm to ambient temperature over 1.5 hours. Evaporate the reaction mixture in vacuo to give the title compound.

EXAMPLE 4

Scheme A, Step d:

(S)-2,2,2-Trichloro-N-(2-chloro-cyclohex-2-enyl)-acetamide

Combine (R)-2,2,2-trichloro-1-(2-chloro-cyclohex-2-enyloxy)-ethylideneamine obtained above and chlorobenzene (200 mL) and heat to 140° C. After 8 hours, evaporate in vacuo to give a residue. Chromatograph on silica gel eluting sequentially with 30% dichloromethane/hexane, 50% dichloromethane/hexane, 70% dichloromethane/hexane, and dichloromethane. Evaporation of the product containing fractions gives a solid. Recrystallize the solid from dichloromethane/hexane to give the title compound as a solid: mp; 78°–79° C. Specific rotation $[\alpha]^2{}_D{}^0 = -77.30°$ (c=0.920, $CHCl_3$).

EXAMPLE 5

Scheme A, Step e:

(S)-2-Chloro-cyclohex-2-enylamine

Combine (S)-2,2,2-trichloro-N-(2-chloro-cyclohex-2-enyl)-acetamide (5.55 g, 20 mmol) and potassium carbonate (5.60 g, 40 mmol) in 1/1 water/methanol (40 mL). Stir at 70° C. for 48 hours. Remove the methanol in vacuo to give the title compound in water solution.

EXAMPLE 6

Scheme A, Step f:

(S)-N-(2-Chloro-cyclohex-2-enyl)-2-[2(S)-1,3-dihydro-1,3-dioxo-isoindol-2-yl)-3-phenyl-propionamide Cool the water solution of (S)-2-chloro-cyclohex-2-enylamine obtained above to 0° C. Add phthalimido-L-phenylalanine acid chloride (23 mL, 27% in ethyl acetate, 20.5 mmol). Allow to warm to ambient temperature over 1 hour. Pour the reaction mixture into dichloromethane and extract with 1M hydrochloric acid and saturated sodium bicarbonate solution. Separate organic layer, dry over $MgSO_4$, filter and evaporate in vacuo to give a solid. Recrystallization from dichloromethane/hexane to give the title compound as a solid: mp; 189°–190° C. Specific rotation $[\alpha]^2{}_D{}^0 = -147.30°$ (c=0.983, $CHCl_3$). Elem. Anal. calculated for $C_{23}H_{20}ClN_2O_3$: C, 67.56; H, 5.18; N, 6.85. Found: C, 7.68; H, 5.13; N, 6.83.

EXAMPLE 7

Scheme A, Step g:

N-[2(S)-[(6-Oxo)-hexanoic acid methyl ester]]-2-[2(S)-1,3-dihydro-1,3-dioxo-isoindol-2-yl)-3-phenyl-propionamide methyl ester Combine (S)-N-(2-chloro-cyclohex-2-enyl)-2-[2(S)-1,3-dihydro-1,3-dioxo-isoindol-2-yl)-3-phenyl-propionamide (0.818 g. 2.0 mmol) in dichloromethane (30 mL) and methanol (20 mL). Cool the solution to −78° C. Pass a stream of ozonized oxygen through the solution until a persistent blue solution was obtained. Pass a stream of nitrogen through the solution until colorless. Add tributylphosphine (1.05 mL, 4.0 mmol) and stir at −70° C. for 30 minutes. Warm to ambient temperature stir for 5 hours. Evaporate in vacuo to give the title compound as a colorless oil.

EXAMPLE 8

Scheme A, Step h:

(S)-1-[2(S)-(1,3-Dihydro-1,3-dioxo-isoindo-2-yl)-1-oxo-3-phenylpropyl] -1,2,3,4-tetrahydro-2-pyridine-carboxylic acid methyl ester Combine the N-[2(S)-[(6-oxo)-hexanoic acid methyl ester]]-2-[2(S)-1,3-dihydro-1,3-dioxo-isoindol-2-yl)-3-phenyl-propionamide methyl ester obtained above as a colorless oil, dichloromethane (70 mL) and trifluoroacetic acid (200 µL). Heat to reflux drying the refluxate by the use of a Dean-Stark trap. After 2 hours, evaporate in vacuo. Chromatograph on silica gel to give the title compound as a solid: mp; 145°–146° C.

Preparation of [4S-[4α, 7α(R*), 12bβ]]-7-[(1-oxo-2(S)-thio- 3-phenylpropyl)amino]-1,2,3,4,6,7,8,12b-octahydro-6-oxo-pyrido[ 2,1-a][2]benzazepine-4-carboxylic acid and [4S-[4α, 7α(R*), 12bβ]]-7-[(1-oxo-2(S)-acetylthio-3-phenylpropyl)amino] -1,2,3,4,6,7,8,12b-octahydro-6-oxo-pyrido[ 2,1-a][2]benzazepine-4-carboxylic acid.

EXAMPLE 9

[4S-[4α, 7α(R*), 12bβ]]-7-[(1,3-Dihydro-1,3-dioxo-2H-isoindol-2-yl)]-1,2,3,4,6,7,8,12b-octahydro-6-oxo-pyrido[2,1-a] [2]benzazepine-4-carboxylic acid, diphenylmethyl ester Combine trifluoromethane sulfonic acid (500 g, 3.33 mole) and trifluoroacetic anhydride (74.8 mL, 0.53 mole) and place under nitrogen atmosphere. Stir and add a solution of (S)-1-[2(S)-(1,3-dihydro-1,3-dioxo-isoindo-2-yl)-1-oxo-3-phenylpropyl] -1,2,3,4-tetrahydro-2-pyridine-carboxylic acid methyl ester (200 g, 0.48 mole) in methylene chloride (1 L) with cooling at such a rate as to keep the pot temperature below 35° C. Stir at ambient temperature for 2 days. Pour into vigorously stirring ice water (5 L) and stir for 30 minutes. Extract with ethyl acetate (3×1 L) combine the organic layers and extract with water (3×500 mL). Evaporate in vacuo to a residue. Dissolve the residue in ethyl acetate (4 L) and extract with ¼ saturated potassium hydrogen carbonate (1 L), then ⅓ saturated potassium hydrogen carbonate (7×1 L). Combine the aqueous extracts and dilute with ethyl acetate (2 L). Stir the resulting mixture and cool to 5°–10° C. Adjust to pH 2 using concentrated hydrochloric acid (about 750 mL).

Separate the organic layer and extract the aqueous phase with ethyl acetate (3×1 L). Combine the ethyl acetate layers, extract with water (3×1 L), then saturated sodium chloride (0.8 L), and dry (MgSO₄), filter and wash with ethyl acetate (3×200 mL). Evaporate in vacuo to leave [4S-[ 4α, 7α(R*), 12bβ]]-7-[(1,3-dihydro-1,3-dioxo-2H-isoindol-2-yl )]-1,2,3, 4,6,7,8,12b-octahydro-6-oxopyrido [2,1-a ][2]benzazepine-4-carboxylic acid as a colorless foam.

Dissolve [4S-[4α, 7α(R*), 12bβ]]-7-[(1,3-dihydro-1,3-dioxo- 2H-isoindol-2-yl)]-1,2,3,4,6,7,8,12b-octahydro-6-oxopyrido[ 2,1-a][2]benzazepine-4-carboxylic acid (113.9 g, 0.28 mole) in methylene chloride (1.2 L) and dry over anhydrous MgSO₄ (60 g). Filter and wash with methylene chloride (3×200 mL). Evaporate in vacuo to a residue. Dissolve the residue in anhydrous dimethylformamide (860 mL) and place under nitrogen atmosphere. Add cesium carbonate (98.9 g, 0.3 mole) in one portion. Stir for 45 minutes at ambient temperature. Add bromodiphenylmethane (164.8 g, 0.67 mole). Stir the resulting mixture at ambient temperature for 18 hours. Quench the reaction with ethyl acetate (2.464 L) and water (630 mL). Separate the organic phase and wash with water (7×625 mL), ¼ saturated potassium hydrogen carbonate (625 mL), water (625 mL), and saturated sodium chloride (625 mL). Dry (MgSO₄), filter and evaporate in vacuo to yield 214.4 g of an oil.

Extract the combined aqueous washings with ethyl acetate (3×500 mL), extract with water (4×300 mL) and dry (MgSO₄). Filter and evaporate in vacuo to yield an additional 20.2 g of an oil.

Dissolve the crude product (234.6 g) in methylene chloride (200 mL) and plug filter through 213 g of silica gel, eluting with methylene chloride (2 L). Boil off the solvent and replace with hexane (3 L), with the pot temperature reaching a maximum of 65° C. Cool to ambient temperature, decant off the precipitated oil and crystallize (9A ethanol) to give the title compound; mp 153°–155° C.

EXAMPLE 10

[4S-[4α, 7α(R*), 12bβ]]-7-(Amino)-1,2,3,4,6,7,8,12b-octahydro- 6-oxopyrido[2,1-a][2]benzazepine-4-carboxylic acid, diphenylmethyl ester Combine [4S-[4α, 7α(R*), 12bβ]]-7-[(1,3-dihydro-1,3-dioxo- 2H-isoindol-2-yl)]-1,2,3,4,6,7,8,12b-octahydro-6-oxopyrido[ 2,1-a][2]benzazepine-4-carboxylic acid, diphenylmethyl ester (170.9 g, 0.3 mole), hydrazine monohydrate (34.4 g, 0.68 mole) and methanol (3.4 L) under nitrogen atmosphere. Heat at reflux for 5 hours. Cool to ambient temperature and filter to remove phthaloyl hydrazide. Evaporate the filtrate in vacuo to a residue and slurry in chloroform (600 mL). Remove insoluble phthaloyl hydrazide by filtration and wash with chloroform (4×210 mL). Extract the filtrate with water (4×429 mL), dry (MgSO₄), and filter. Evaporate the filtrate to a solid residue of the title compound.

EXAMPLE 11

[4S-[4α, 7α(R*), 12bβ]]-7-[(1-Oxo-2(S)-acetyloxy-3-phenylpropyl)amino] -1,2,3,4,6,7,8,12b-octahydro-6-oxopyrido[ 2,1-a][2]benzazepine-4-carboxylic acid, diphenylmethyl ester Combine (S)-3-phenyllactic acid (11.17 g, 67.2 mmol) and sulfuric acid (0.3 mL of a 10% solution in acetic acid). Add acetic anhydride (6.34 mL, 67.2 mmol) over 10 minutes. Warm to 90° C. with stirring for 45 minutes. Allow to cool, pour into diethyl ether and extract with water three times. Separate the organic layer, dry (MgSO₄) and concentrate in vacuo to yield (S)-3-phenyl-2-acetyloxypropionic acid as a white oil.

Combine (S)-3-phenyl-2-acetyloxypropionic acid (3.6 g, 17 mmol) and [4S-[4α, 7α(R*), 12bβ]]-7-(amino)- 1,2,3,4, 6,7,8,12b-octahydro-6-oxopyrido[2,1-a] [2]benzazepine-4-carboxylic acid, diphenylmethyl ester (7.6 g, 17 mmol) in methylene chloride (50 mL). Add EEDQ (4.3 g, 17 mmol). Stir for 18 hours at ambient temperature under argon atmosphere. Extract with 2N hydrochloric acid, separate the organic layer, extract with water, then with saturated sodium hydrogen carbonate. Dry (MgSO₄) and concentrate in vacuo to yield an off-white foam. Purify by silica gel chromatography (30%, then 40%, then 50% ethyl acetate/hexane) to give the title compound.

EXAMPLE 12

[4S-[4α, 7α(R*), 12bβ]]-7-[(1-Oxo-2(S)-hydroxy-3-phenylpropyl)amino] -1,2,3,4,6,7,8,12b-octahydro-6-oxo-pyrido[ 2,1-a][2]benzazepine-4-carboxylic acid, diphenylmethyl ester Dissolve [4S-[4α, 7α(R*), 12bβ]]-7-[(1-oxo-2(S)-acetyloxy- 3-phenylpropyl)amino]-1,2,3,4,6,7,8,12b-octahydro- 6-oxo-pyrido[2,1-a][2]benzazepine-4-carboxylic acid, diphenylmethyl ester (11.0 g, 17.4 mmol) in ethanol (75 mL) and tetrahydrofuran (40 mL) and add lithium hydroxide (22 mL, 1M solution in water, 22 mmol). Stir the reaction mixture for 2 hours. Remove the solvent in vacuo at 35° C. and partition the residue between ethyl acetate and 1M hydrochloric acid. Separate the organic phase, dry (MgSO$_4$), and concentrate in vacuo. Purify by silica gel chromatography (1:1/tetrahydrofuran:hexane) to give the title compound.

Elem. Anal. Calcd. for C$_{37}$H$_{36}$N$_2$O$_5$: C, 75.49; H, 6.16; N, 4.76; Found: C, 75.30; H, 6.44; N, 4.54.

EXAMPLE 13

[4S-[4α, 7α(R*), 12bβ]]-7-[(1-oxo-2(R)-acetyloxy-3-phenylpropyl)amino] -1,2,3,4,6,7,8,12b-octahydro-6-oxo-pyrido[ 2,1-a][2]benzazepine-4-carboxylic acid, diphenylmethyl ester Dissolve [4S-[4α, 7α(R*), 12bβ]]-7-[(1-oxo-2(S)-hydroxy- 3-phenylpropyl)amino]-1,2,3,4,6,7,8,12b-octahydro-6-oxopyrido[ 2,1-a][2]benzazepine-4-carboxylic acid, diphenylmethyl ester (59 mg, 0.1 mmol), triphenylphosphine (39 mg, 0.15 mmol) and acetic acid (8.7 µL, 0.15 mmol) in anhydrous tetrahydrofuran (3 mL). Treat with DIAD (32 mg, 0.15 mmol) at 0° C. Stir for 5 minutes at 0° C., then allow to stir at ambient temperature for 45 minutes. Remove the volatiles in vacuo and purify the residue by silica gel chromatography (3:1/hexane:tetrahydrofuran) to give the title compound.

EXAMPLE 14

[4S-[4α, 7α(R*), 12bβ]]-7-[(1-Oxo-2(R)-hydroxy-3-phenylpropyl)amino] -1,2,3,4,6,7,8,12b-octahydro-6-oxo-pyrido[ 2,1-a][2]benzazepine-4-carboxylic acid, diphenylmethyl ester Dissolve [4S-[4α, 7α(R*), 12bβ]]-7-[(1-Oxo-2(R)-acetyloxy- 3-phenylpropyl)amino]-1,2,3,4,6,7,8,12b-octahydro-6-oxo-pyrido[2,1-a][2]benzazepine-4-carboxylic acid, diphenylmethyl ester (366 mg, 0.58 mmol) in methanol (5 mL) and tetrahydrofuran (5 mL) and add lithium hydroxide (0.8 mL, 1M solution in water, 0.8 mmol). Stir the reaction mixture for 2 hours and remove the solvent in vacuo. Acidify and partition between methylene chloride and water. Separate the organic phase, dry (MgSO$_4$) and concentrate in vacuo to give a white foam.

In another run, dissolve [4S- 4α, 7α(R*), 12bβ]]-7-[(1-oxo- 2(R)-acetyloxy-3-phenylpropyl )amino]-1,2,3,4,6,7,8, 12b-octahydro- 6-oxo-pyrido[2,1-a][2]benzazepine-4-carboxylic acid, diphenylmethyl ester (100 mg, 0.16 mmol) in methanol (5 mL) and tetrahydrofuran (5 mL) and add lithium hydroxide (0.2 mL, 1M solution in water, 0.2 mmol). Stir the reaction mixture for 1 hour, dilute with water (50 mL), make acidic and extract with diethyl ether (50 mL). Separate the organic phase, extract with water (2×50 mL), dry (MgSO$_4$) and concentrate in vacuo.

Combine the material from both runs and purify by silica gel chromatography (30%, then 50% tetrahydrofuran/hexane) to give of the title compound as a white foam.

EXAMPLE 15

[4S-[4α, 7α(R*), 12bβ]]-7-[(1-Oxo-2(S)-acetylthio-3-phenylpropyl)amino] -1,2,3,4,6,7,8,12b-octahydro-6-oxo-pyrido[ 2,1-a][2 ]benzazepine-4-carboxylic acid, diphenylmethyl ester Combine DIAD (31 mg, 0.15 mmol), triphenylphosphine (39 mg, 0.16 mmol) and anhydrous tetrahydrofuran (2 mL). Cool to 0° C. and stir for 30 minutes under an argon atmosphere. Add the [4S-[4α, 7α(R*), 12bβ]]-7-[(1-oxo-2(R)-hydroxy- 3-phenylpropyl)amino] -1,2,3,4,6,7,8,12b-octahydro-6-oxo-pyrido[ 2,1-a][2]benzazepine-4-carboxylic acid, diphenylmethyl ester (59 mg, 0.1 mmol) as a solid, then immediately add thiolacetic acid (11 µL, 0.15 mmol). Allow the reaction to warm to ambient temperature and stir overnight. Remove the solvent in vacuo and purify the residue by silica gel chromatography (40% ethyl acetate/hexane then 50% ethyl acetate/hexane) to give the title compound.

EXAMPLE 16

[4S-[4α, 7α(R*), 12bβ]]-7-[(1-Oxo-2(S)-acetylthio-3-phenylpropyl)amino] -1,2,3,4,6,7,8,12b-octahydro-6-oxo-pyrido[ 2,1-a][2]benzazepine-4-carboxylic acid Dissolve [4S-[4α, 7α(R*), 12bβ]]-7-[(1-oxo-2(S)-acetylthio-3-phenylpropyl)amino]-1,2,3,4,6,7,8,12b-octahydro- 6-oxo-pyrido[2,1-a][2]benzazepine-4-carboxylic acid, diphenylmethyl ester (51 mg, 0.079 mmol) in anisole (4 drops) and trifluoroacetic acid (1 mL) under argon atmosphere at ambient temperature. Allow to stand for 45 minutes, remove the trifluoroacetic acid in vacuo and purify by silica gel chromatography (50 mL of 40% ethyl acetate/hexane then 50 mL of 40% ethyl acetate/hexane with 5% acetic acid added) to give the title compound.

EXAMPLE 17

Preparation of [4S-[4α, 7α(R*), 12bβ]]-7-[(1-Oxo-2(S)-thio- 3-phenylpropyl)amino]-1,2,3,4,6,12b-octahydro-6-oxo-pyrido[ 2,1-a][2]benzazepine-4-carboxylic acid Dissolve [4S-[4α, 7α(R*), 12bβ]]-7-[(1-oxo-2(S)-acetylthio- 3-phenylpropyl)amino]-1,2,3,4,6,7,8,12b-octahydro- 6-oxo-pyrido[2,1-a][2]benzazepine-4-carboxylic acid (57 mg, 0.12 mmol) in deoxygenated methanol (3 mL) containing lithium hydroxide (0.25 mL, 1M in water, 0.25 mmol). Stir for 30 minutes under argon atmosphere at ambient temperature. Reduce in volume to 1.5 mL in vacuo, then add, by dropwise addition, to a rapidly stirring solution of 2M hydrochloric acid (2 mL). Collect the resulting precipitate, wash with water and dry in a vacuum dessicator for 1 hour. Dry at 35° C. overnight to give the title compound as a white electrostatic powder.

What is claimed is:

1. The compound (S)-2,2,2-trichloro-N-(2-chloro-cyclohex- 2-enyl)-acetamide.

2. The compound (R)-2,2,2-trichloro-N-(2-chloro-cyclohex- 2-enyl)-acetamide.

\* \* \* \* \*